United States Patent [19]

Lamb et al.

[11] Patent Number: 5,176,906
[45] Date of Patent: Jan. 5, 1993

[54] FLUORESCENT ORGANOSILICON COMPOUNDS AND METHODS

[75] Inventors: Jo A. Lamb; Maris J. Ziemelis, both of Midland, Mich.

[73] Assignee: Dow Corning Corporation, Midland, Mich.

[21] Appl. No.: 517,893

[22] Filed: May 2, 1990

[51] Int. Cl.$^5$ .............................................. A61K 7/075
[52] U.S. Cl. ...................................... 424/70; 424/7.1; 252/551; 556/425; 558/25; 558/26
[58] Field of Search ........................... 424/70, 7.1, 47; 252/551; 556/425; 558/25, 26

[56] References Cited

U.S. PATENT DOCUMENTS 4,595,586  6/1986  Flom ........................................ 424/47
4,732,201  3/1988  Robbins et al. ............. 252/DIG. 14
4,866,152  9/1989  Lamb et al. ........................... 528/25

Primary Examiner—Thurman K. Page
Assistant Examiner—D. Colucci
Attorney, Agent, or Firm—Jim L. DeCesare

[57] ABSTRACT

A fluorescent organosilicon compound derived from the reaction of an aminofunctional organopolysiloxane and a fluorescent labeling reagent in which the fluorescent labeling reagent is incorporated into the molecule of the aminofunctional organopolysiloxane by means of a sulfonamide linkage. A method of treating hair is also dislcosed in which the fluorescent organosilicon compound is applied to hair and the treated hair is examined for fluorescence under ultraviolet light in order to determine the extensiveness of deposition of the fluorescent organosilicon compound.

10 Claims, No Drawings

FLUORESCENT ORGANOSILICON COMPOUNDS AND METHODS

BACKGROUND OF THE INVENTION

This invention relates to certain fluorescent organosilicon compounds and to the use of such compounds for the treatment of hair. More particularly, the invention relates to aminofunctional siloxanes rendered fluorescent by reaction of the siloxanes with certain fluorescent labeling reagents.

The molecules of certain inorganic and organic substances when irradiated with radiant energy of sufficient intensity and appropriate wavelength absorb energy and then these excited molecules immediately emit radiant energy of a longer wavelength. This phenomenon is called fluorescence. Fluorescence spectra are uniquely characteristic of the molecular energy levels of the molecules emitting the absorbed radiant energy. The intensity of this fluorescence is proportional to the concentration of the fluorescent substance. A spectrofluorometer or spectrophotometer equipped with a fluorescence attachment can be used to obtain the excitation spectrum and emission spectrum of a fluorescent substance. The fluorescence excitation spectrum is obtained by irradiating a sample with energy of different wavelengths while measuring the intensity of the emission fluorescence at a fixed wavelength. Numerous materials exhibit fluorescence including materials otherwise known as fluorescent dyes and pigments such as optical brighteners, fluorescent labeling reagents, laser dyes, and spin labels. These materials respond only to ultraviolet radiation in contrast to those materials otherwise known as daylight fluorescent pigments.

Fluorescent organosilicon compounds are not new. For example, fluorescent aminofunctional polysiloxanes are disclosed in U.S. Pat. No. 4,866,152, issued Sep. 12, 1989. The fluorescent siloxanes in the '152 patent are formed by reacting the aminofunctional polyorganosiloxanes with certain optical brightening agents which are specifically fluorescent functional organosulfonic acids and fluorescent functional organoaldehydes. The compounds of the present invention, however, are not produced by employing optical brightening agents but rather fluorescent materials of a different nature such as fluorescent labeling reagents. Thus, new compositions are disclosed herein which are distinct from those compositions taught in the '152 patent.

SUMMARY OF THE INVENTION

This invention relates to a fluorescent organosilicon compound derived from the reaction of an aminofunctional organopolysiloxane and a fluorescent labeling reagent.

The invention is also directed to a fluorescent organosilicon compound derived from the reaction of an aminofunctional organopolysiloxane and a fluorescent labeling reagent in which the fluorescent labeling reagent is incorporated into the molecule of the aminofunctional organopolysiloxane by means of a sulfonamide linkage.

The invention is further related to a method of treating hair by applying to the hair a fluorescent organosilicon compound derived from the reaction of an aminofunctional organopolysiloxane and a fluorescent labeling reagent, and including the step of examining the treated hair for fluorescence under ultraviolet light in order to determine the extensiveness of deposition of the fluorescent organosilicon compound.

These and other features, objects, and advantages, of the herein described present invention will become more apparent from a consideration of the following detailed description thereof.

DETAILED DESCRIPTION OF THE INVENTION

Certain amine functional siloxanes are known to provide excellent hair conditioning when applied to hair after the hair has been shampooed. These amine functional siloxanes are useful as after-shampoo hair conditioners because the siloxanes facilitate combing and impart a smooth feel to hair. Shampoos have also been formulated which include amine functional siloxanes and these shampoo-conditioners are said to provide improved fullness and body to hair. One particular unique advantage of the amine functional siloxane in the treatment of hair is the substantivity of the amine functional siloxane for the substrate which provides durable hair treatments. However, since these amine functional siloxanes are clear fluids, it is difficult to determine visually the exact extensiveness of deposition on the hair of the amine functional siloxane in order to provide maximum coverage and benefit. In accordance with the present invention, however, not only do the amine functional siloxanes provide the above advantages as hair conditioning agents, but in addition are capable of indicating visually the extensiveness of deposition on hair when exposed to a source of ultraviolet light.

Organopolysiloxanes of the present invention are amine-functional organopolysiloxanes which consist of a plurality of organosiloxane units of the general formula

$$R_aSiO_{(4-a-b)/2} \atop X_b \qquad (I)$$

wherein X is a reactive amine-functional organic group bearing at least one —NHR″ group, in which R″ is hydrogen or an alkyl radical having 1 to 6 carbon atoms. On average, at least two reactive X groups per molecule of organopolysiloxane are required to be within the scope of the present invention.

In the above formula, R is a non-reactive group which may be independently selected from alkyl radicals having 1 to 6 carbon atoms, such as methyl, ethyl, propyl, butyl, isopropyl or hexyl radicals. The R group may also be selected from monovalent cycloaliphatic radicals, such as cyclopentyl, cyclohexyl, or cyclooctyl radicals. Alternatively, R can be an aryl group such as phenyl, benzyl, styryl, tolyl and xenyl. Still further, R may be a monovalent halohydrocarbyl group having 1 to 6 carbon atoms such as 3,3,3-trifluoropropyl, 3-chloropropyl or perfluorobutylethyl. Finally, R may be a monovalent haloaromatic group such as 2,4-dichlorophenyl. It is preferred that R is selected from methyl, phenyl or 3,3,3-trifluoropropyl radicals. In any given organosiloxane unit, the value of a may be 0, 1, 2 or 3, the value of b may be 0, 1, or 2 and the sum (a+b) is less than 4.

In a preferred embodiment of this invention, the X group is —R′(NHCH$_2$CH$_2$)$_g$NR″H. In this embodiment, R′ is a divalent hydrocarbon group having from 3 to 6 carbon atoms such as trimethylene, tetramethylene or isobutylene. Preferably, R′ is trimethylene or isobutylene. R'' is hydrogen or an alkyl radical having from 1 to 6 carbon atoms, preferably hydrogen, and g is an integer having a value from zero to 4. Preferably, g is one.

It is further preferred that the amine-functional organopolysiloxane be a linear copolymer selected from structures which may be represented by the average formulae

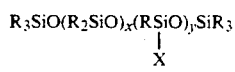  (II)

or

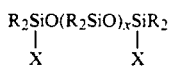  (III)

wherein the R groups are independently selected from the non-reactive species enumerated above, the average value of x may vary from zero to about 1000 and the average value of y may vary from 2 to about 100. It is also preferred that the R groups are methyl radicals and X is —R'(NHCH$_2$CH$_2$)$_g$NR''H, as defined above. In these embodiments, particularly preferred X groups are

—CH$_2$CH$_2$CH$_2$NCH$_2$CH$_2$NH$_2$
           |
           H

—CH$_2$CH$_2$CH$_2$NH$_2$

—CH$_2$CH$_2$CH$_2$NH(CH$_3$)

and

—CH$_2$CHCH$_2$NH(CH$_3$)
      |
      CH$_3$ while the most preferred X group is X', which may be represented by the formula

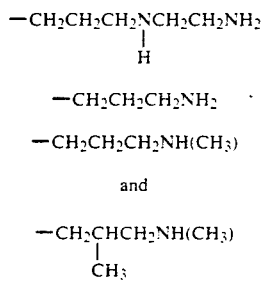

(Group X')

The most preferred amine-functional organopolysiloxanes have the structure

Me$_3$SiO(Me$_2$SiO)$_x$(MeSiO)$_y$SiMe$_3$  (IV)
                    |
                    X' wherein X' has been defined and Me hereinafter denotes the methyl radical. In this case, x represents the average number of dimethyl units and can range from zero to about 1,000, preferably from 50 to 500. Likewise, y represents the average number of methyl-aminofunctional units and can range from 2 to about 100, preferably from 2 to 30. These amine-functional siloxanes are fluids having a viscosity between about 20 and 4,000 cP at 25° C.

The amine-functional organopolysiloxanes of this invention are well known in the art and are available commercially. Accordingly, no detailed description as to their preparation has been included herein.

Fluorescent labeling reagents which may be used in accordance with the present invention are, for example, compounds such as 4-dimethylaminoazobenzene-4'-sulfonyl chloride; 1-dimethylaminonaphthalene-5-sulfonamidoethyltrimethylammonium perchlorate known as dansyl aminoethyltrimethylammonium perchlorate; N-1-dimethylaminonaphthalenesulfonyl aziridine known as dansyl aziridine; 5-dimethylaminonaphthalene-1-sulfonyl chloride known as dansyl chloride; 5-dimethylaminonaphthalene-1-sulfonyl fluoride known as dansyl fluoride; 5-dimethylaminonaphthalene-1-sulfonyl hydrazide known as dansyl hydrazine; 3-5-dimethylamino-1-naphthalenesulfonamido-proxyl; 3-5-dimethylamino-1-naphthalenesulfonamido-2,2,5,5-tetramethyl-1-pyrrolidinyloxy; 1-2-5-dimethylaminonaphthalene-1-sulfonyl-aminoethylamino-3-1-naphthaleneoxy-2-propanol; 4-dimethylamino-1-naphthylisothiocyanate; and fluorescamine. The term dansyl, it is noted, is the abbreviation for 5-dimethylaminonaphthalene-1-sulfonyl. The preferred fluorescent compound in accordance with the concepts of the present invention is dansyl chloride of the formula $(CH_3)_2NC_{10}H_6SO_2Cl$. This material is well known in the art and has various utilities including its use as a reagent for fluorescent labeling of amines, amino acids, proteins, and phenols. It also yields fluorescent peptide derivatives.

The fluorescent labeling reagent is incorporated into the organosilicon compound by means of a sulfonamide linkage which effectively bonds the fluorescent labeling reagent to the aminofunctional siloxane molecule. This mechanism is illustrated in the following reaction sequence:

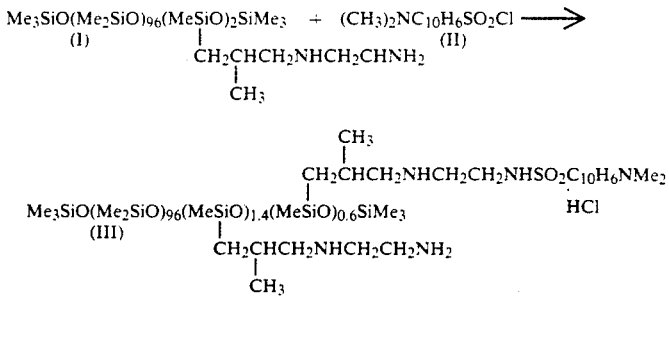

The following example illustrates a procedure for the preparation of fluorescent compounds in accordance with the concepts of the present invention.

EXAMPLE I

Into a container was placed 2.12 grams of 5-dimethylaminonaphthalene-1-sulfonyl chloride known as dansyl chloride. This compound is shown in the above reaction sequence as (II). Compound (II) was dissolved in fifty grams of toluene. Into a five hundred milliliter round bottom flask was placed 96.66 grams of the amine functional siloxane (I) shown in the above reaction sequence. The solution of toluene and 5-dimethylaminonaphthalene-1-sulfonyl chloride was added to the round bottom flask containing compound (II) and stirring was maintained with a magnetic stirring bar. A condenser was attached to the flask and the contents of the flask was heated to reflux for thirty minutes. The product was stripped on a rotary evaporator at eighty degrees Centigrade to remove the toluene. A light yellow-green fluid was obtained and identified as compound (III) as shown in the above reaction sequence.

EXAMPLE II

The fluorescent aminofunctional siloxane obtained from Example I was tested in order to demonstrate the utility of the compound as an indicator of the efficacy and the extensiveness of a hair treatment application. Tresses of European human hair were employed. A solution was prepared containing a two percent by weight concentration of compound (III) in a polydimethylcyclosiloxane fluid having a viscosity of 4.2 centistokes measured at twenty-five degrees Centigrade. One gram of the treatment solution was sprayed onto two tresses of hair. The treated hair tresses were dried at room temperature for twenty-four hours. The tresses were examined under a source of ultraviolet light and were found to be fluorescent, indicating that the had been effective. It was observed that compound (III) had deposited more extensively on damaged ends of the individual hair tresses.

It will be apparent from the foregoing that many other variations and modifications may be made in the compounds, compositions, and methods, described herein, without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. A method of treating hair comprising applying to the hair a fluorescent organosilicon compound derived from the reaction of an aminofunctional organopolysiloxane and a fluorescent labeling agent, the fluorescent labeling agent being a dansyl derivative.

2. The method of claim 1 in which the fluorescent labeling reagent is selected from the group consisting of 1-dimethylaminonaphthalene-5-sulfonamidoethyltrimethylammonium perchlorate,
N-1-dimethylaminonaphthalenesulfonyl aziridine,
5-dimethylaminonaphthalene-1-sulfonyl chloride,
5-dimethylaminonaphthalene-1-sulfonyl fluoride, and
5-dimethylaminonaphthalene-1-sulfonyl hydrazide.

3. The method of claim 2 in which the fluorescent labeling reagent is
5-dimethylaminonaphthalene-1-sulfonyl chloride having the formula $(CH_3)_2NC_{10}H_6SO_2Cl$.

4. The method of claim 1 in which the aminofunctional organopolysiloxane includes a plurality of independently selected units of the formula

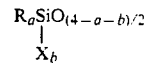

wherein X is an amine-functional organic group bearing at least one —NHR" group, in which R" is hydrogen or an alkyl radical having 1 to 6 carbon atoms, R is a group selected from alkyl, cycloalkyl, haloalkyl, aromatic or haloaromatic radicals, a has a value of 0, 1, 2, or 3, b has a value of 0, 1 or 2, and the sum (a+b) is less than 4, there being on average at least two X groups per molecule of said amine-functional organopolysiloxane.

5. The method of claim 4 wherein said R groups are independently selected from methyl, phenyl or 3,3,3-trifluoropropyl radicals.

6. The method of claim 5 wherein said X group is represented by the formula —R'(NHCH$_2$CH$_2$)$_g$NR"H in which R' is a divalent hydrocarbyl group having 3 to 6 carbon atoms, R" is selected from hydrogen or an alkyl radical having 1 to 6 carbon atoms and g is an integer having a value of zero to 4.

7. The method of claim 1 wherein said organopolysiloxane is selected from linear copolymers having the average structure

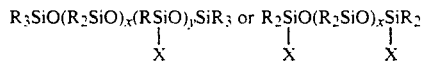

in which the average value of x can vary from zero to about 1000 and the average value of y can vary from 2 to about 100.

8. The method of claim 7 wherein said R groups are independently selected from methyl, phenyl or 3,3,3-trifluoropropyl radicals.

9. The method of claim 8 wherein said X group is represented by the formula —R'(NHCH$_2$CH$_2$)$_g$NR"H in which R' is a divalent hydrocarbyl group having 3 to 6 carbon atoms, R" is selected from hydrogen or an alkyl radical having 1 to 6 carbon atoms and g is an integer having a value of zero to 4.

10. The method of claim 1 including the step of examining the treated hair for fluorescence under ultraviolet light in order to determine the extensiveness of deposition of the fluorescent organosilicon compound.

* * * * *